(12) United States Patent
Benkowski et al.

(10) Patent No.: US 6,652,447 B2
(45) Date of Patent: Nov. 25, 2003

(54) METHOD OF CONTROLLING AN IMPLANTABLE PUMP SYSTEM

(75) Inventors: Robert J. Benkowski, Houston, TX (US); Gino F. Morello, Leonia, NJ (US)

(73) Assignee: MicroMed Technology, Inc., Houston, TX (US)

(*) Notice: Subject to any disclaimer, the term of this patent is extended or adjusted under 35 U.S.C. 154(b) by 55 days.

(21) Appl. No.: 09/777,073

(22) Filed: Feb. 5, 2001

(65) Prior Publication Data

US 2001/0037093 A1 Nov. 1, 2001

Related U.S. Application Data

(62) Division of application No. 09/165,840, filed on Oct. 2, 1998, now Pat. No. 6,183,412.
(60) Provisional application No. 60/060,665, filed on Oct. 2, 1997.

(51) Int. Cl.[7] ................................. A61M 1/10
(52) U.S. Cl. ............................................. 600/16
(58) Field of Search ............... 600/16, 17, 18; 623/3.1, 3.11–3.19, 3.2–3.26; 604/65

(56) References Cited

U.S. PATENT DOCUMENTS

| | | | | |
|---|---|---|---|---|
| 4,016,871 A | * | 4/1977 | Schiff | 128/2.06 R |
| 5,108,360 A | * | 4/1992 | Tachi | 600/16 |
| 5,113,869 A | * | 5/1992 | Nappholz et al. | 128/696 |
| 5,569,156 A | * | 10/1996 | Mussivand | 600/16 |
| 5,711,753 A | * | 1/1998 | Pacella et al. | 600/16 |
| 5,713,856 A | * | 2/1998 | Eggers et al. | 604/65 |

* cited by examiner

*Primary Examiner*—George R. Evanisko
*Assistant Examiner*—Frances P. Oropeza
(74) *Attorney, Agent, or Firm*—Howrey Simon Arnold & White LLP

(57) ABSTRACT

A controller module for an implantable pump system which has a pump motor includes a processor, a motor controller electrically coupled to the processor and adapted to power the pump motor such that the pump motor operates at a desired speed. The motor controller outputs digital representations of the pump motor operating parameters to the processor. A first memory device is coupled to the processor for storing the digital signals representing the pump motor operating parameters. The controller module further includes a user interface. The controller module may be coupled to a data acquisition system, which provides power and exchanges data with the controller module. The controller module may alternately be coupled to a home support system which provides power for the controller module and storage for system components.

4 Claims, 10 Drawing Sheets

METHOD OF CONTROLLING AN IMPLANTABLE PUMP SYSTEM

CROSS-REFERENCE TO RELATED APPLICATION

This application is a divisional of application Ser. No. 09/165,840, filed Oct. 2, 1998, now U.S. Pat. No. 6,183,412, which claims the benefit of U.S. Provisional Patent Application No. 60/060,665, entitled "Implantable Pump System," filed Oct. 2, 1997, by the same inventors, which is incorporated herein by reference in its entirety.

BACKGROUND OF THE INVENTION

1. Field of the Invention

The invention relates generally to pump control systems and, more specifically, to a pump control system for an implantable blood pump.

2. Description of Related Art

Implantable blood pump systems are generally employed either to completely replace a human heart that is not functioning properly, or to boost blood circulation in patients whose heart still functions but is not pumping blood at an adequate rate. Known implantable blood pump systems are primarily used as a "bridge to transplant." In other words, existing blood pump system applications are mainly temporary fixes, intended to keep a patient alive until a donor is available. However, the shortage of human organ donors, coupled with improvements in blood pump reliability make long-term, or even permanent blood pump implementations a reality. The estimated need for a relatively simple, long-term ventricle assist device (VAD) is presently projected at between 50,000 and 100,000 patients per year in the United States alone.

Despite this need, existing implantable pump systems have not been satisfactory for long term use. Known systems of the continuous flow type are designed primarily for use in a hospital setting. These systems typically include the implanted pump device, a power source such as a rechargeable battery, a motor controller for operating the pump motor, and an external operator console. While some existing implantable pump systems allow for operation while decoupled from the operator console, operating these systems "stand-alone" can be a risky endeavor. This is due, at least in part, to the lack of an adequate user interface when the system is decoupled from the console.

Prior art blood pump systems generally only include electronics for operating the pump when disconnected from the console. Often, the user interface is limited to a green light indicating that the system is operating, or a red light indicating that the system is not operating properly. There are no provisions for displaying system parameters, diagnostic messages, alarm messages, etc. Further, known systems typically lack memory capabilities. Hence, when a technician attempts to diagnose a prior art blood pump system after the red light indicated a system failure, there is no record of the system conditions related to the failure.

Further, even when an implantable continuous flow pump is coupled to an operator console, relevant system parameters are missing. For example, the operator consoles of known continuous flow pump systems may monitor pump parameters such as voltage level, current level, pump speed, etc. These parameters, however, do not provide all the necessary information to properly monitor a system that is as complicated as the human circulatory system. The system can be better assessed if pump parameters are analyzed in conjunction with other factors, such as blood flow rate, blood pressure or vibro-acoustic signatures. It is even more desirable to monitor all of these parameters together in real time. Unfortunately, known blood pump systems typically lack the ability to integrally analyze these data in real time.

Moreover, prior blood pump systems are not conducive to long-term use outside an institutional setting. As discussed above, known systems require a large, fixed operator console for the system to function. While prior art operator consoles may be cart mounted to be wheeled about the hospital, at home use of known systems is difficult at best.

Other problems of prior pump systems that have limited their mobility and use to relatively short times are related to motor controller size and shape limitations necessary for convenient mobility, weight limitations for implantation to avoid tearing of implant grafts due to inertia of sudden movement, high power consumption that requires a larger power supply, complex Hall Effect sensors/electronics for rotary control, the substantial desire for minimizing percutaneous (through the skin) insertions, including support lines and tubes, and high cost effectively.

Thus, there is a need for an implantable pump control system that addresses the shortcomings associated with the prior art.

SUMMARY OF THE INVENTION

A controller module for an implantable pump system which includes a pump having an electric motor is presented in one aspect of the present invention. The controller module includes a microprocessor, a motor controller electrically coupled to the microprocessor and adapted to power the pump motor such that the pump motor operates at a desired speed. The motor controller outputs digital representations of the pump motor operating parameters to the microprocessor. A first memory device is coupled to the microprocessor for storing the digital signals representing the pump motor operating parameters. The controller module further includes a user interface. In one embodiment, the user interface includes an LCD display and a keypad. In a further embodiment, a rechargeable battery is included for powering the controller module.

In another aspect of the present invention, a data acquisition system includes a primary power supply and a computer. The data acquisition system is adapted to be removably coupled to the controller module such that the power supply provides power to the controller module when the data acquisition device is coupled to the controller module. The computer is programmed to exchange data with the controller module when the data acquisition device is coupled to the controller module.

In yet another aspect of the invention, a patient home support system includes a power supply and a battery charger adapted to receive and charge the rechargeable battery. A first connector is adapted to removably couple the home support system to the controller module such that the power supply provides power to the controller module when the home support device is coupled to the controller module.

In a still further aspect of the invention, a method of controlling an implanted pump includes the acts of coupling a controller module to the implanted pump. The controller module includes a microprocessor, a display device, a user input device, and a digital memory. The method further includes collecting operating parameters of the implanted pump, displaying the collected parameters on the display device as selected by a user via the input device, storing the collected parameters in the digital memory, and displaying the stored parameters on the display device as selected by a user via the input device.

BRIEF DESCRIPTION OF THE DRAWINGS

Other objects and advantages of the invention will become apparent upon reading the following detailed description and upon reference to the drawings in which:

FIG. 3 is a block diagram of the controller module of an embodiment of the invention;

Figure 1:
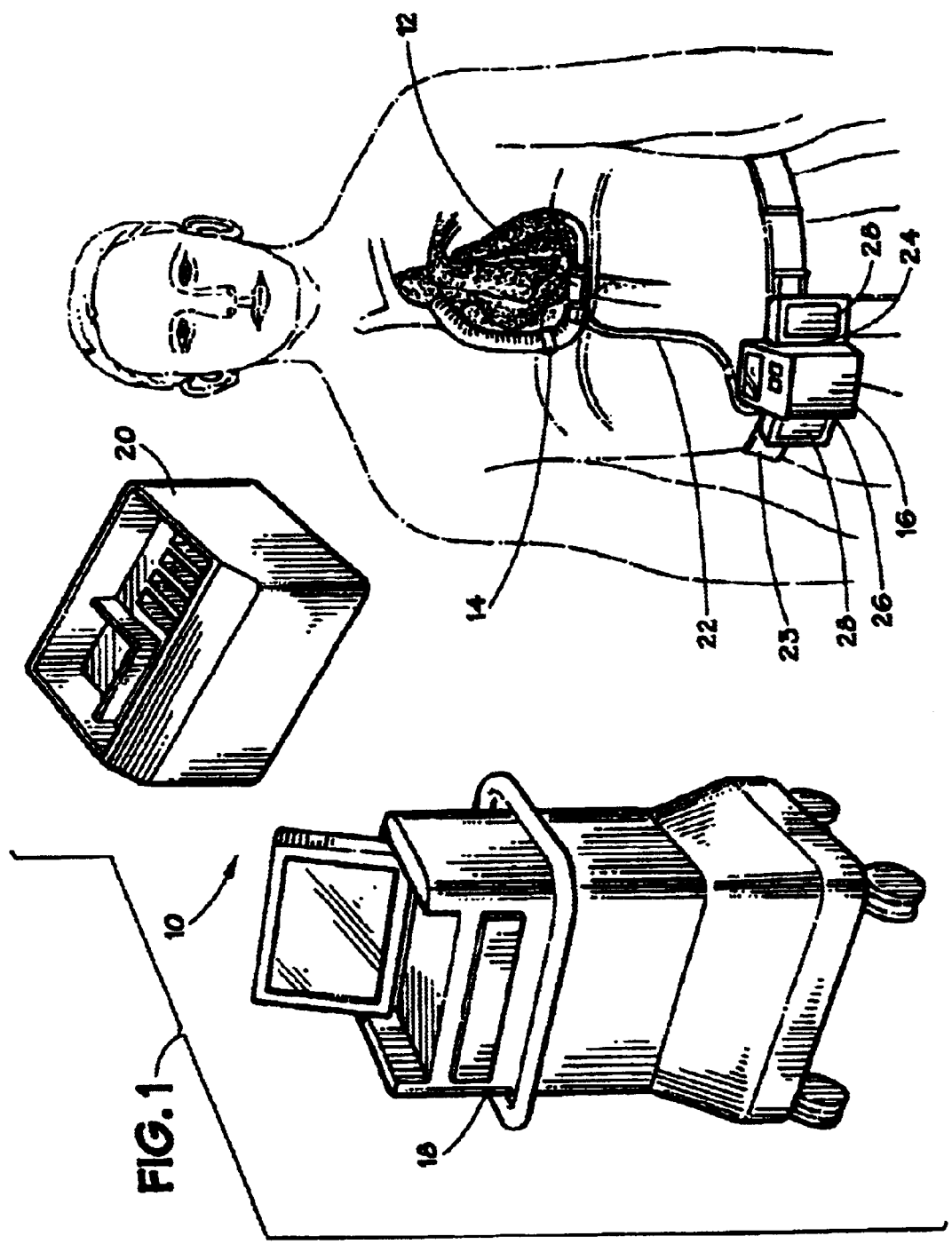
FIG. 1 is a block diagram of a ventricle assist device (VAD) system in accordance with an embodiment of the invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

System Overview

Turning to the figures, and in particular to FIG. 1, a ventricle assist device (VAD) system 10 in accordance with an embodiment of the present invention is illustrated. The VAD system 10 includes components designed to be implanted within a human body and components external to the body. The components of the system 10 that are implantable include a rotary pump 12 and a flow sensor 14. The external components include a portable controller module 16, a clinical data acquisition system (CDAS) 18, and a patient home support system (PHSS) 20. The implanted components are connected to the controller module 16 via a percutaneous cable 22. The controller module 16 may be mounted to a support device, such as a user's belt 23 or to a vest worn by the user. Alternatively, the controller module 16 may be placed on the CDAS 18 or placed on a nightstand when the user is in bed. A spare controller module 16 may be stored in the PHSS 20. The controller module 16 includes two connectors 24 and 26 for coupling to one or more batteries 28, which provide power for the controller module 16 when in a stand-alone mode. The system 10 may further include a battery charger (not shown in FIG. 1). The same connectors 24, 26 also may couple the controller module to either the CDAS 18 or PHSS 20.

In an embodiment of the invention, the system 10 is controlled in an open loop fashion where a predetermined speed is set and the flow rate varies according to the pressure differential across the pump 12. The pump 12 is controlled in a closed loop fashion, wherein the actual pump speed is fed back to the controller module 16, which compares the actual speed to the desired predetermined speed and adjusts the pump 12 accordingly.

In other embodiments, the controller module 16 is programmed such that closed loop, physiologic control methods are implemented by the system 10. In one embodiment, the controller module 16 may vary the pump 12 speed according to the cardiac cycle (triggered either by electrical sensors or by real-time analysis of the pump 12 speed (RPM) or current). In one implementation, the pump 12 is used in conjunction with a valve in the graft coupled to the implanted pump 12 outflow. The pump speed is increased synchronously with the heart during systole since high pump speed while the valve is closed would waste energy. In another implementation, a mean low flow through the pump 12 is desired, for example, 2–3 liters per minute, and there is no valve in the outflow graft. At this condition, the pump speed is too low to stop the negative flow through the pump during diastole, so it would be desirable to increase the pump speed asynchronously with the heart to prevent this reverse flow and still maintain a relatively low mean flow.

The controller module may further be used for much lower frequency physiologic control as compared to the implementations described above. This lower frequency control adjusts the pump 12 for events such as sleeping, normal activity or high energy exertion. In these cases, the pump 12 average speed is adjusted in order to adjust the mean flow through the pump 12. Alternately, the high and low frequency control schemes may be combined, employing high frequency control based on each cardiac cycle and low frequency control based on blood flow requirements. Still further, the controller module 16 may used in conjunction with a cardiac output measuring device. The controller module 16 may be programmed with cycles to incrementally reduce the pump speed when the cardiac output measuring device determines to what extent the patient's heart has recovered while being assisted.

VAD Pump

The system 10 of an embodiment of the invention may incorporate an implantable continuous-flow blood pump 12, such as the various embodiments of axial flow pumps disclosed in U.S. Pat. No. 5,527,159 or in U.S. Pat. No. 5,947,892, both of which are incorporated herein by reference in their entirety. An implantable centrifugal pump also would be suitable for use in other embodiments of the invention. In still further embodiments, pulsatile pumps are employed.

Figure 2:
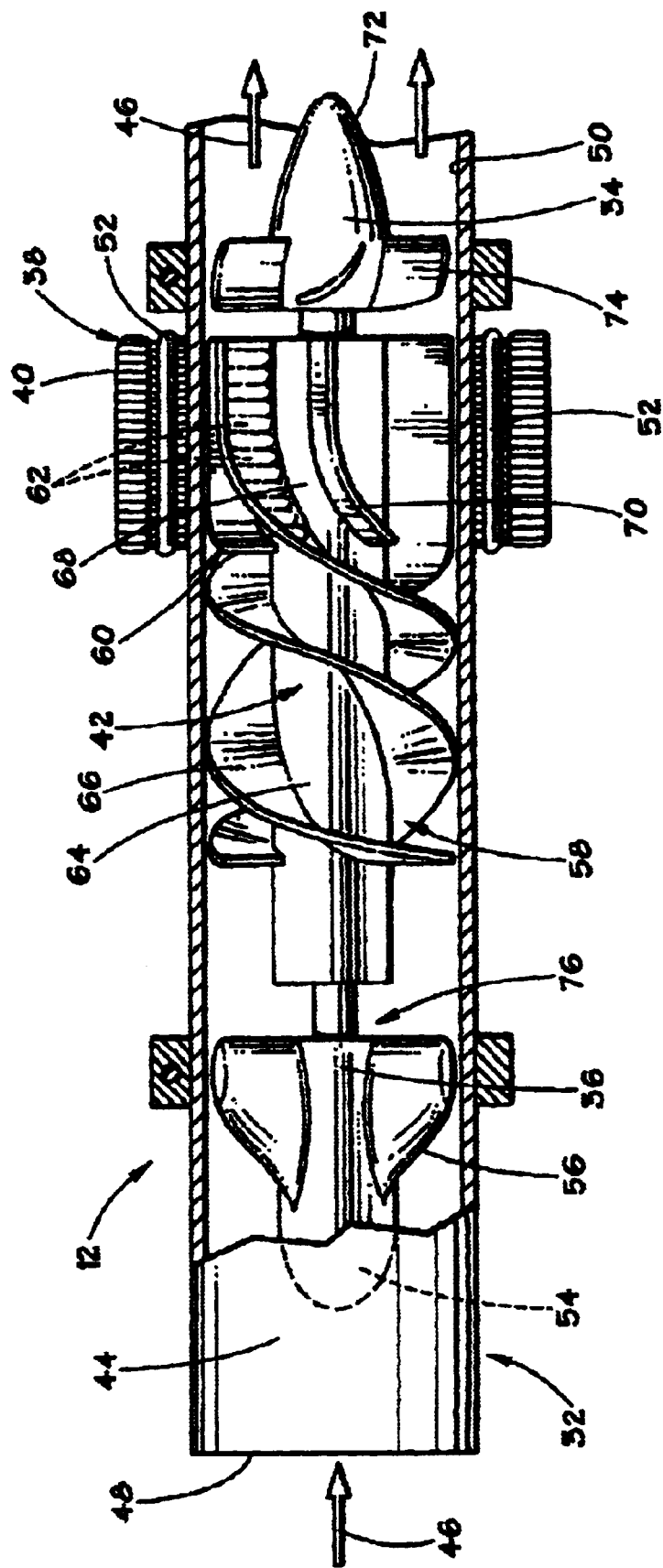
FIG. 2 illustrates an implantable heart pump in accordance with one embodiment of the invention.

An example of a blood pump 12 suitable for use in an embodiment of the invention is illustrated in FIG. 2. The exemplary pump includes a pump housing 32, a diffuser 34, a flow straightener 36, and a brushless DC motor 38, which includes a stator 40 and a rotor 42. The housing 32 includes a flow tube 44 having a blood flow path 46 therethrough, a blood inlet 48, and a blood outlet 50.

The stator 40 is attached to the pump housing 32, is preferably located outside the flow tube 44, and has a stator field winding 52 for producing a stator magnetic field. In one embodiment, the stator 40 includes three stator windings and may be three phase "Y" or "Delta" wound. The flow straightener 36 is located within the flow tube 44, and includes a flow straightener hub 54 and at least one flow straightener blade 56 attached to the flow straightener hub 54. The rotor 42 is located within the flow tube 44 for rotation in response to the stator magnetic field, and includes an inducer 58 and an impeller 60. Excitation current is applied to the stator windings 52 to generate a rotating magnetic field. A plurality of magnets 62 are coupled to the rotor 42. The magnets 62, and thus the rotor 42, follow the rotary field to produce rotary motion.

The inducer 58 is located downstream of the flow straightener 36, and includes an inducer hub 64 and at least one inducer blade 66 attached to the inducer hub 64. The impeller 60 is located downstream of the inducer 58, and includes an impeller hub 68 and at least one impeller blade 70 attached to the impeller hub 68. The diffuser 34 is located within the flow tube 44 downstream of the impeller 60, and includes a diffuser hub 72 and at least one diffuser blade 74 attached to the diffuser hub 72. The exemplary pump further includes a front bearing assembly 76 attached to the flow straightener hub 36.

Controller Module

Figure 4:
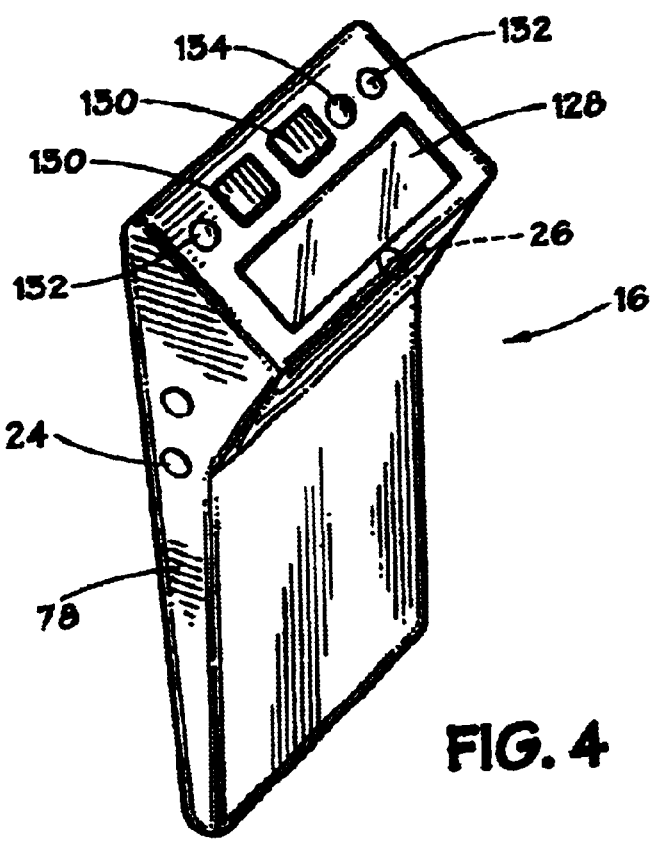
FIG. 4 is a perspective view of an exemplary controller module case.

The controller module 16 of an embodiment of the present invention is illustrated in greater detail in FIG. 3 in block diagram form. In one embodiment of the invention, the controller module 16 is packaged in an ergonomic case 78 as illustrated in FIG. 4.

The controller module 16 includes a processor, such as a microcontroller 80, which in one embodiment of the invention is a model PIC16C77 microcontroller manufactured by Microchip Technology. The microcontroller 80 is coupled to a communications device 81 such as an RS-232 driver/receiver as is known in the art, and a hardware clock and calendar device 82, which contains clock and date information, allowing the controller module 16 to provide real-time clock and calendar information. The microcontroller 80 communicates with the hardware clock 82 via the I²C protocol. The microcontroller 80 also is programmed with a selftest routine, which is executed upon application of power to check components of the controller module 16.

The controller module 16 includes first and second connectors 24, 26 for coupling is the controller module 16 to a power source, such as a battery 28, or the CDAS 18 or PHSS 20. In an embodiment of the invention, the connectors 24, 26 include a break-away feature, such that the connectors 24, 26 disengage themselves if a given force is applied. For example, if a battery pack connected to the controller module 16 falls on the floor, the connector will disengage rather than pull the controller module and in turn, tug on the percutaneous cable.

Figure 5:
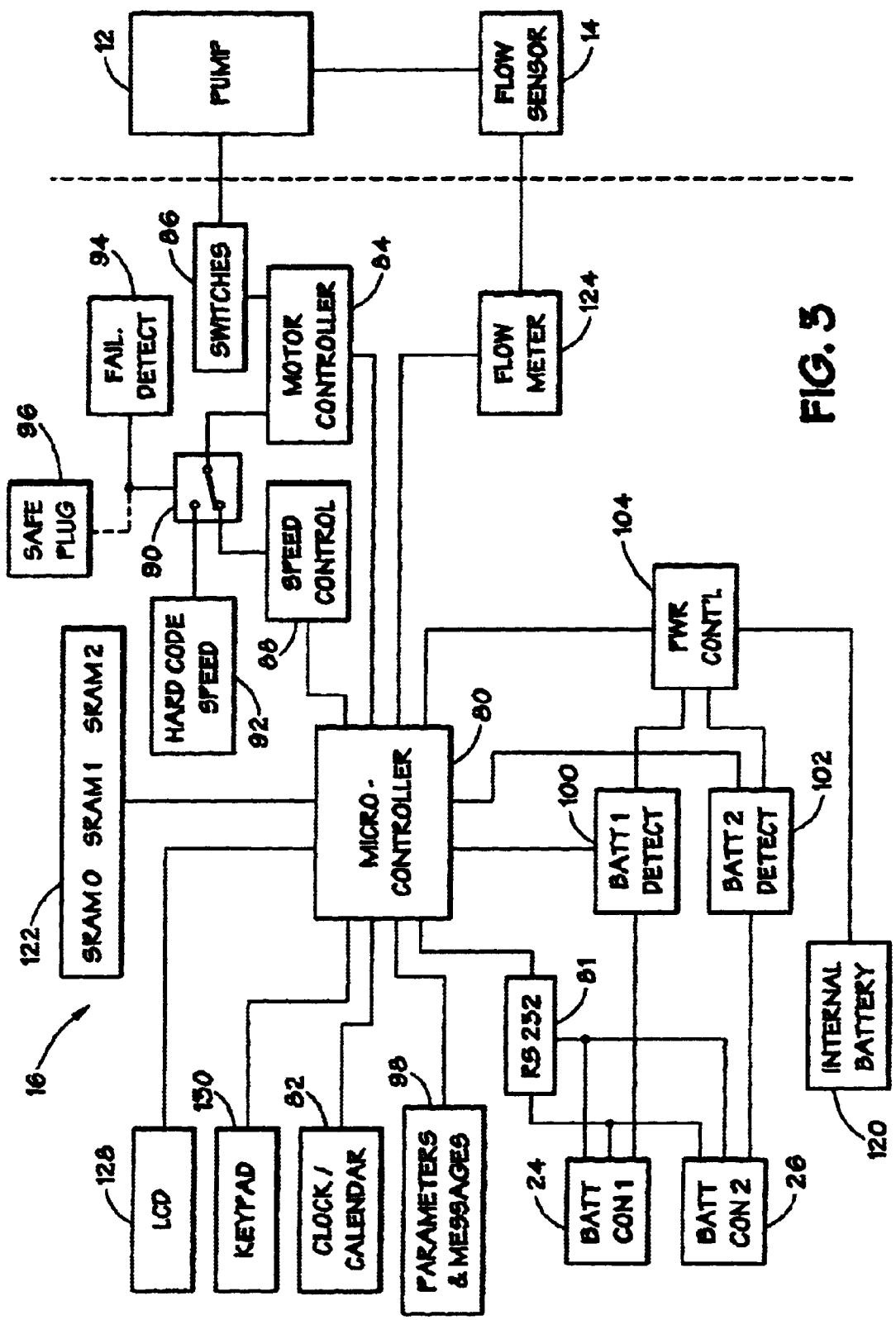
FIG. 5 illustrates a vest in accordance with an embodiment of the invention for holding components of the implantable pump system.

In one embodiment of the invention, the controller module 16 and the batteries 28 are contained in a support device comprising a vest 210 worn by the patient, illustrated in FIG. 5. The vest 210 includes a first pocket 212 for holding the controller module 16 and two battery pouches 214 for holding two batteries 28. The battery pouches 214 may include integral connectors 216 adapted to receive and connect the batteries 28 to cables 218 which are coupled to the controller module connectors 24, 26. The cables 218 may be internal to the vest 210, accessible through openings secured by a fastener, such as a Velcro fastener (not shown). The battery pouches 214 also include covers 220 to further protect the batteries 28 held within the battery pouches 214. A particular embodiment includes a PHSS connector on one of the battery pouches 214, to which a cable connects to couple the controller module 16 to the PHSS 20. In other embodiments, the controller module 16 and the batteries 28 are adapted to be connected to a belt worn by the patient, and in still further embodiments, the belt may include suspenders attached thereto to provide support for the belt.

Motor Controller

A motor controller 84 is coupled to the microcontroller 80, and the motor controller 84 is coupled to the pump 12. The operation of the brushless DC motor 38 of the present invention requires that current be applied in a proper sequence to the stator windings 52. Two stator windings 52 have current applied to them at any one time, and by sequencing the current on and off to the respective stator windings 52, a rotating magnetic field is produced. In an embodiment of the invention, the motor controller 84 senses back electro motive force (EMF) voltage from the motor windings 52 to determine the proper commutation phase sequence using phase lock loop (PLL) techniques. Whenever a conductor, such as a stator winding 52, is "cut" by moving magnetic lines of force, such as are generated by the magnets 62 of the brushless DC motor 38, a voltage is induced. The voltage will increase with rotor speed 42. It is possible to sense this voltage in one of the three stator windings 52 because only two of the motor's windings 52 are activated at any one time, to determine the rotor 42 position.

An alternative method of detecting the rotor 42 position relative to the stator 40 for providing the proper stator winding 52 excitation current sequence is to use a position sensor, such as a Hall effect sensor (not shown). However, adding additional components, such as Hall effect sensors, requires additional space, which is limited in any implanted device application. Further, using a position detection device adds sources of system failures.

The motor controller 84 switches a series of power switching devices 86 to regulate the stator winding 52 current. In one embodiment, the power switching devices 86 comprise metal oxide semiconductor field effect transistors (MOSFETs).

The embodiment illustrated in FIG. 3 further includes a pump motor speed control circuit 88 coupled to the microcontroller 80 to receive inputs regarding pump operation parameters. The speed control circuit 88 is coupled to the motor controller 84 through a switching device 90, which couples either the speed control circuit 88 or a hardware-implemented "safe mode" speed setting 92, which is independent of the microcontroller 80.

The switching device 90 is actuated by a microprocessor failure detector 94, which may comprise an external "watchdog" timer (not shown in FIG. 3) such as a monostable multivibrator, which continuously monitors the microcontroller 80. Any watchdog timers internal to the microcontroller 80 are disabled. Alternatively, the switching device 90 may be actuated by a safety plug 96 which is adapted to plug into either of the controller module connectors 24, 26. The external watchdog timer is periodically reset by the microcontroller 80 during normal controller module 16 operation.

In the event that the microcontroller 80 fails, the watchdog timer will not be reset. Upon the watchdog timer expiration, the watchdog timer activates the switching device 90, bypassing the microcontroller 80 and setting the pump 12 to a predetermined speed setting 92. This insures that the pump 12 continues to operate. In a further embodiment, the watchdog timer, upon sensing a failure, triggers an emergency clamp and shuts down the pump 12. The emergency clamp prevents backward flow through the pump 12.

Figure 6:
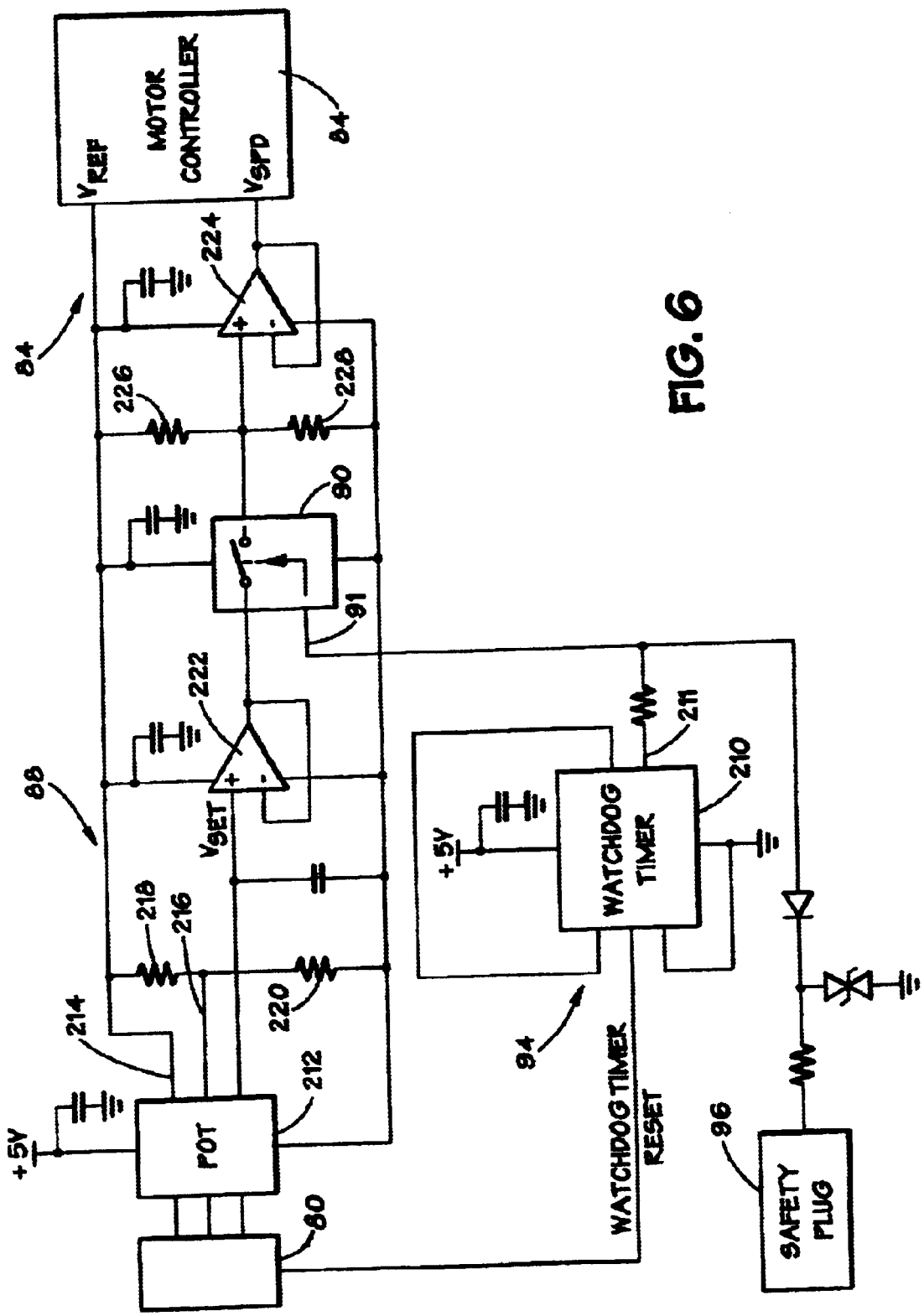
FIG. 6 illustrates an embodiment of a motor speed control circuit in accordance with an embodiment of the invention.

FIG. 6 illustrates a schematic diagram of a motor control circuit 200 in accordance with an exemplary embodiment of the invention. The motor speed control circuit 200 includes the motor controller 84, the speed control circuit 88, the fail detector 94, the switching device 90 and the hard code speed 92 from FIG. 3.

The failure detector 94 includes a watchdog timer 210 coupled to the switching device 90. Suitable watchdog timers and switching devices include, for example, a model MAX705 monostable multivibrator and a model MAX4514 single pole-single throw CMOS analog switch, respectively, both available from Maxim Integrated Products. In operation, the output of the watchdog timer 210 is logically high during normal system operation (the microcontroller 80 functioning properly), and logically low when a malfunction or failure of the microcontroller 80 is detected.

During normal operation, the microcontroller 80 periodically provides a watchdog timer reset signal to the input of the watchdog timer 210, which resets the watchdog timer 210, and forces its output 211 logically high. The output 211 of the watchdog timer is coupled to the control input 91 of the switching device 90. In the exemplary embodiment illustrated in FIG. 6, the switching device 90 is configured as a normally open switch. Therefore, the logically high signal at the control input 91 maintains the switching device 90 in a closed state, allowing the microcontroller 80 to control the pump 12 in accordance with user input. If the watchdog timer 210 does not receive its periodic watchdog timer reset signal, after a predetermined time period (for example, one second), it will time-out and its output 211 will toggle from a logically high state to a logically low state. The logically low state at the control input 91 of the switching device 90 will decouple the microcontroller 80 from the motor controller 84 by opening the switching device 90. Alternatively, the switching device 90 may be operated by the safety plug 96 to manually decouple the microcontroller 80 from the motor controller 84.

In the embodiment illustrated in FIG. 6, the motor controller 84 comprises a Micro Linear model ML4425 motor controller. The motor controller 84 includes a voltage controlled oscillator, a pulse width modulated speed control circuit, a commutation logic control circuit, a pulse width modulated current control circuit, MOSFET drivers, a back EMF sampler circuit, and a power fail detector. Additional details regarding the features and operation of the Micro Linear ML4425 motor controller are available in the appropriate Micro Linear specification sheet.

The motor controller 84 further includes an onboard voltage reference $V_{ref}$ and a speed control voltage input $V_{spd}$ that is used as the control reference voltage input for the motor speed control phase-locked loop (PLL). In a typical implementation of a motor controller such as the Micro Linear ML4425 motor controller, predetermined voltage levels of $V_{spd}$ correspond to desired motor speeds, and the voltage level corresponding to the desired motor speed is input to the speed control voltage input $V_{spd}$. With typical motor controller chips, however, motor speed control is based, at least in part, on the relationship between the onboard voltage reference $V_{ref}$ and the speed control voltage input $V_{spd}$. In an embodiment employing the Micro Linear ML4425 motor controller, in accordance with the circuit shown in FIG. 6, the onboard voltage reference $V_{ref}$ output varies from 6.5 volts to 7.5 volts (6.9 volts nominal). Thus, if absolute voltage levels corresponding to desired motor speeds are input to the speed control voltage input $V_{spd}$, the actual pump motor speed may vary as much as ±20%.

To reduce this variation, the speed control circuit 88 shown in FIG. 6 provides a speed control voltage input $V_{spd}$ level that is programmed to some proportion of the onboard voltage reference $V_{ref}$ value, rather than an absolute voltage level. This removes the motor speed control's dependency on the onboard voltage reference $V_{ref}$ output. In a particular embodiment of the invention, this reduces the pump motor speed error from ±20% to approximately ±1%.

In the embodiment illustrated in FIG. 6, the speed control 88 includes a digitally programmable electronic potentiometer 212 that receives inputs from the microcontroller 80. A model X9312T nonvolatile digital potentiometer available from Xicor, Inc. is a suitable digital potentiometer. The "high" terminal 214 of the potentiometer 212 is directly coupled to the onboard voltage reference $V_{ref}$ output of the motor controller 84, and the "low" terminal 216 is coupled to the onboard voltage reference $V_{ref}$ through a voltage divider comprising resistors 218, 220. In a specific embodiment, the resistors 218, 220 comprise 1.02 kΩ and 1.5 kΩ resistors, respectively. The potentiometer 212 thus provides a voltage output $V_{set}$ at its "wiper" terminal that varies from about $0.6 \times V_{ref}$ to $V_{ref}$. Allowing the speed control voltage input $V_{spd}$ to equal the potentiometer 212 output voltage $V_{set}$ yields a pump motor speed range of about 7,500 RPM to 12,500 RPM.

The potentiometer 212 output voltage $V_{set}$ is coupled to an input of a first unity gain buffer amplifier 222, the output of which is coupled, during normal operations, through the switching device 90 to an input of a second unity gain buffer amplifier 224. The output of the second unity gain buffer amplifier 224 is connected to the $V_{spd}$ input of the motor controller 84 via a resistive divider comprising resistors 226, 228. The values of resistors 226, 228 should be selected so as to achieve two desired ends: 1.) minimize the loading of the $V_{set}$ signal when the microcontroller 80 is operating normally, and the switching device 80 is therefore closed; and 2.) provide the proper $V_{spd}$ voltage to realize the desired "safe mode" pump motor speed when the switching device 90 is opened via the watchdog timer 210 or the safety plug 96. In one particular embodiment, the predetermined "safe mode" speed setting is 8,500 RPM. Hence, the resistors 226, 228 comprise 31.6 kΩ and 66.5 kΩ resistors, respectively, to achieve a $V_{set}$ value equal to $0.68 \times V_{ref}$ when the switching device 90 is open.

The microcontroller 80 may further be programmed with a pump restart feature for restarting the pump 12 in the event of a pump failure. The pump restart leaves the motor speed preset to its latest value. When the restart is activated, the microcontroller 80 initiates a start-up sequence of the motor controller 84, and locks a predetermined time period of pump performance data into the controller module's memory. The controller module memory is discussed further below. If the pump 12 successfully restarts in response to the pump restart feature within a given time limit (10 seconds in one embodiment), a diagnostic alarm is enabled and the motor controller 84 returns the pump 12 to the latest preset speed. If the pump 12 fails to restart, an emergency alarm is enabled and the restart sequence repeats. The microcontroller 80 may be programmed to limit the number of restart attempts. In a particular embodiment, the controller module 16 limits the number of restart attempts to three for a given pump stoppage.

The microcontroller 80 includes a multiple channel analog to digital (A/D) converter, which receives indications of motor parameters from the motor controller 84. Thus, the controller module 16 may monitor parameters such as instantaneous motor current, the AC component of the motor current, and motor speed. In an embodiment of the invention, the controller module 16 incorporates low pass digital filtering algorithms to calculate the mean values of parameters such as motor current to an accuracy of ±1% of full scale.

The controller module 16 may include a ventricle collapse feature which detects excessive pump suction using the AC component of the motor current parameter, wherein the microcontroller 80 is programmed to detect an excessive suction condition and in response thereto, reduce the pump rate until the condition is eliminated, or until the minimum pump speed is reached. The excessive pump suction detection feature discriminates between a normal motor current wave form (quasi-sinusoidal after filtering) and a suspect wave form (predictably distorted). Alternately, variations in motor speed may be used to detect excess suction. Excessive pump suction parameters may be stored in an electrically erasable programmable read only memory (EEPROM) 98 coupled to the microcontroller 80.

Controller Module Power

The controller module 16 receives power from the battery 28, the CDAS 18 or the PHSS 20 (see FIG. 1). The controller module 16 includes first and second connectors 24, 26, both of which are capable of coupling the battery 28 (which may be rechargeable), the CDAS 18 or the PHSS 20 to the controller module 16. In one embodiment of the invention, the batteries 28 comprise Duracell DR36 Powersmart Batteries, which include an indicator that provides the battery's relative and absolute charge levels, and an internal memory that stores battery data, including the number of charge and discharge cycles, the battery time remaining, etc. The controller module 16 microcontroller 80 is programmed to query the battery 28 to obtain data related to the battery. Thus, the microprocessor may be programmed to display an alarm message when a battery reaches a minimum charge or time level, or if a battery has not had a desired number of charge and discharge cycles.

The first and second connectors 24, 26 have first and second battery detect circuits 100, 102, respectively, coupled thereto. The battery detect circuits 100, 102 sense whether a battery 28, the CDAS 18 or PHSS 20, or nothing is coupled to the connector 24, 26. The battery detect circuits 100, 102 are coupled to a power source control circuit 104. If either the CDAS 18 or PHSS 20 is coupled the connectors 24, 26, the power source control circuit 104 detects this and switches the system such that the CDAS 18 or PHSS 20, as applicable, provides power to the controller module 16. If the batteries 28 are coupled to both connectors 24, 26, the battery 28 having the lower charge level (above a minimum level) is selected.

Figure 7:
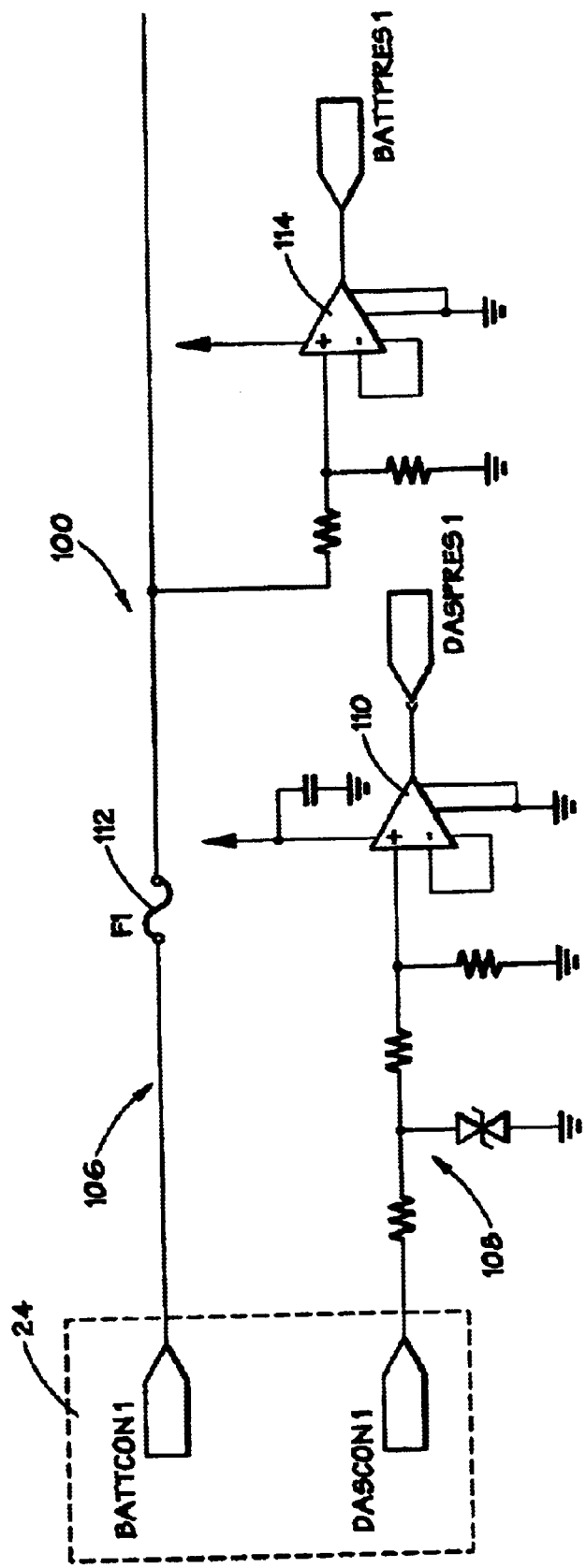
FIG. 7 illustrates an embodiment of a battery detect circuit in accordance with an embodiment of the invention.

An embodiment of a battery detect circuit 100, 102 is illustrated in FIG. 7, which includes a battery detect portion 106 and a DAS detect portion 108. The DAS detect portion 108 detects whether the CDAS 18 or PHSS 20 is coupled to the connector. The DAS detect portion 108 receives a first DAS connect input signal (DASCON1) from the first system connector 24. The DASCON1 signal input is provided to a first comparator 110, which outputs a signal (DASPRES1) indicating whether the CDAS 18 or PHSS 20 is connected to the terminal. If the CDAS 18 or PHSS 20 is coupled to the connector 24, DASPRES1 outputs a logically high signal, and a logically low signal is output if no device is coupled to the connector 24. Similarly, in the battery detect portion 106 of the circuit 100, a first battery connect input signal (BATTCON1) is coupled through a fuse 112 to an input of a second comparator 114, which outputs a signal (BATTPRES1) that is logically high if a battery 28 is coupled to the connector and above a predetermined minimum charge level. The BATTPRES1 signal is logically low if there is no battery 28 present, or if the battery 28 is below the minimum charge level. The first and second comparators 110, 114 may comprise two comparators of an LTC1443 quad comparator available from Linear Technology Corp. The remaining two comparators may be used for the second battery detect circuit 102.

Figure 8:
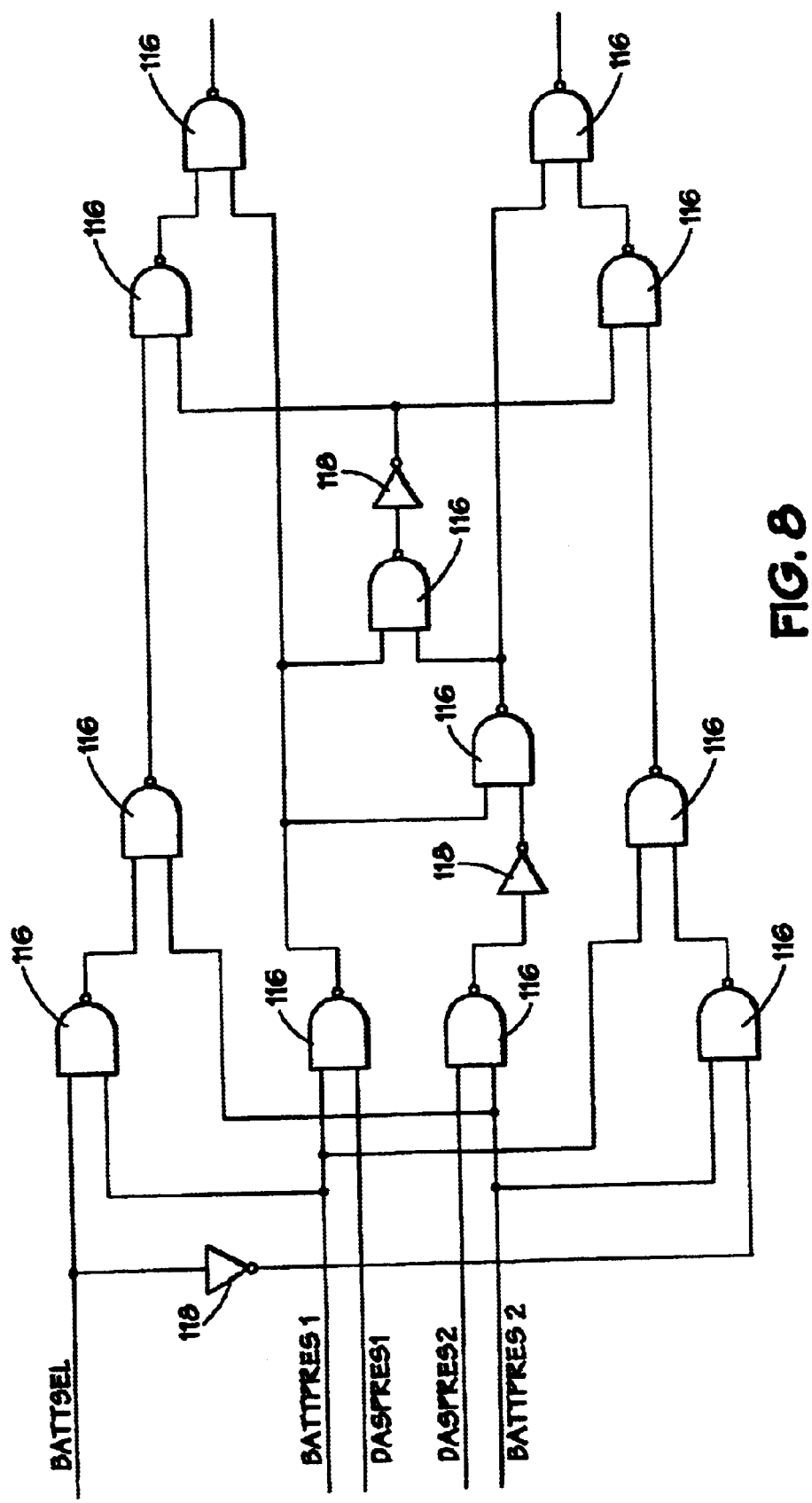
FIG. 8 illustrates an embodiment of a power source control circuit in accordance with an embodiment of the invention.

An embodiment of the power source control circuit 104 is illustrated in FIG. 8. The exemplary logic circuit 104 comprises a plurality of two-input NAND gates 116 and a plurality of inverters 118. For the circuit illustrated in FIG. 8, three 74HC00 quad NAND chips supply the NAND gates 116, and a 74HC04 inverter chip supplies the inverters 118. Inputs to the logic circuit 104 include the DASPRES1 and BATTPRES1 signals from the first battery detect circuit 100, DASPRES2 and BATTPRES2 signals from the second battery detect circuit 102, and a battery select signal (BATTSEL). In other embodiments, the power source control circuit 104 is implemented in software using a programmable logic device.

The BATTSEL signal is provided by the microcontroller 80. If each of the connectors 24, 26 has a battery 28 attached, the microcontroller 80 monitors the connected batteries 28 and selects the battery 28 with the lower charge, as read from the battery pack, if the charge level is above a desired, predetermined level. The microcontroller 80 communicates with the batteries 28 via the I²C protocol. The microcontroller 80 queries the batteries 28 periodically to determine charge status. In an embodiment of the invention, the batteries 28 are queried upon connection and at intervals of approximately one minute thereafter. If the lower charged battery 28 falls below the minimum level, the power source control 104 switches to the higher charged battery 28. If the battery 28 coupled to the first connector 24 is to be selected, the microcontroller 80 outputs a BATTSEL signal that is logically high, and if the battery 28 coupled to the second connector 26 is to be selected, BATTSEL is logically low. Moreover, if the microcontroller 80 determines that one or both batteries 28 fall below a given charge level, the microcontroller 80 may be programmed to shut down selected components of the system 10, such as the flow meter 124, to conserve power.

The power source control circuit 104 provides two output signals, SELECT1 and SELECT2, which in response to the DASPRES1, BATTPRES1, DASPRES2, BATTPRES2 and BATTSEL input signals, indicate whether the controller module 16 is to be powered by the device coupled to the respective connector 24, 26. If the device coupled to the first connector 24 is selected to power the controller module 16, the SELECT1 signal is logically high and the SELECT2 signal is logically low. Conversely, the SELECT1 signal is logically low and the SELECT2 signal is logically high if power is to be provided via the second connector 26. The power source control 104 includes two switching devices (not shown) coupled to the SELECT1 and SELECT2 output terminals and responsive thereto for connecting the controller module 16 to either the first or second connector 24, 26.

Referring again to FIG. 3, an internal battery 120 provides limited back-up power in the event of a complete power loss.

In one embodiment, the internal battery 120 powers the microcontroller 80 and alarms if power from the external batteries 28 is lost, and the internal battery 120 also powers the clock/calendar 82 and the system prompts 98 if the external batteries 28 are disconnected. Thus, power remains available to critical functions and to activate an alarm signaling the loss of power.

Controller Module Memory

As shown in FIG. 3. a series of memory devices 122 are additionally coupled to the microcontroller 80 to save system parameters in the event of an emergency, such as a pump shutdown. In one embodiment of the invention, the memory devices comprise three 128K banks of SRAM, which store pump parameters such as pump voltage, current, RPM and flow. The first of the three SRAM banks, segment 0, is the "looping bank," which employs a continuous, circular buffer that continuously stores the current performance data. Upon a predetermined event, such as a pump shutdown and restart, the microcontroller 80 is programmed to transfer the data from the circular buffer to one of the other memory banks.

The second SRAM bank, segment 1, contains the pump performance data prior to the first alarm or restart that occurs after initial power-on or a clearing of segment 0 by the CDAS (CDAS communications with the controller module will be further discussed below). The third bank, segment 2, contains pump performance data prior to the most recent restart event. After each restart event (or any alarm if segment 0 is clear) the data in the active looping bank are transferred to segment 0 or segment 1, as appropriate. For example, following initial start-up, if the pump stops, the processor transfers the data from the memory segment 0, the circular buffer, to memory segment 1. Assume that the pump then restarts. The pump performance data in the circular buffer associated with any subsequent predetermined events are transferred from memory segment 0 to segment 2, such that segment 2 always has the data associated with the most recent pump event.

In one embodiment of the invention, memory segments 0 and 1 each store 55 seconds of pump performance data segments, including pump speed (RPM), voltage, flow rate, instantaneous motor current and time. Further, sample rates for these parameters may be as follows: instantaneous motor current, 2000 samples per second; flow rate, 333 samples per second; pump speed, 10 samples per second; and voltage, 10 samples per second. The sampling resolution for these parameters is eight bits in one embodiment of the invention.

Each memory segment includes predetermined boundaries for each sampled parameter. For example, pump motor current requires 110,000 bytes to store 55 seconds at 2000 samples per second which may be stored in a predetermined memory array. Defining parameter boundaries in this fashion allows a technician to request parametric data by reading a range of blocks. The last block in each memory segment contains time stamp information available from the real-time clock and calendar along with a start and stop memory pointer for each parameter.

Flow Meter

Another novel aspect of an embodiment of the present invention is the inclusion of an integral flow meter 124, as shown in FIG. 3. As disclosed above, at least one flow sensor 14 is implanted down stream of the pump 12. Alternately, a flow sensor 14 may be integrated with the pump 12. A Custom 12A dual channel flow sensor available from Transonic Systems, Inc. is implanted downstream of the pump 12 in an embodiment of the invention. The flow meter 124, which may comprise a Transonic Systems, Inc. model FPT110 dual channel flow meter, is coupled between the implanted flow sensor 14 and the microcontroller 80. The flow meter 124 averages the data from the two flow sensor channels and outputs flow rate data to the microprocessor A/D converter (not shown), allowing the microprocessor to monitor instantaneous flow rate. The flow signal amplitude of each flow meter channel is also provided to the microprocessor to monitor system integrity.

Since the implanted flow sensor 14 is coupled to the flow meter 124 of the controller module 16, a true measure of system performance (flow rate) is available for analysis, in addition to pump parameters such as pump speed. Further, since the flow meter 124 is an integral component of the controller module 16, flow rate may be displayed on the controller module display (described below), and flow rate data may be saved in the controller module memory 122 for later analysis.

Providing a flow meter 124 as an integral component of the portable controller module 16 solves a significant shortcoming of prior art VAD and artificial heart systems, which typically do not capture and display flow rate data on a portable device. Even if a known VAD or artificial heart system were to include an implanted flow transducer, prior art systems would require an external console to display and capture the flow data. This valuable system information would be lost whenever the system is not coupled to the external console. On the other hand, the present invention provides a means to display and analyze flow rate data for all pump operating times, whether or not the controller module is connected to the CDAS.

Controller Module User Interface

The EEPROM 98 connected to the microcontroller 80, in addition to storing excessive suction detection parameters, stores prompts and messages for display and manipulation via a user interface 126 (not shown in FIG. 3). The microprocessor communicates with the EEPROM 98 via the I²C protocol in one embodiment. As shown in FIG. 4, the user interface 126 may comprise a display 128 and an input device 130. In one embodiment, the controller module display 128 comprises a two-row, back-lit 16-character LCD display; two multicolored LEDs 132 which indicate battery status; and an additional LED 134 which indicates when the unit is in the safemode. The input device 130 may include a keypad, which in an embodiment of the invention, includes two sealed keypad switches to perform the functions of alarm silence and display scroll. The LCD 128 also contains a conventional backlight (not shown), which is automatically lit either by pressing one of the keypad switches 130 or when an alarm is sounded. The LCD 128 is positioned within the controller module case 78 such that it is easily viewed by a user looking down at the controller module 16 mounted on the user's belt or held within the vest 210, or from a bedside when the controller module 16 is located on a table or nightstand.

The display 128 may be configured to display messages in multiple languages. The message displays may be arranged such that predetermined display character positions are reserved for displaying the parameter or alarm "label," such as "PUMP SPEED." These labels may be stored in one or more languages in the message and parameter EEPROM 98. Other predetermined positions on the display 128 may be reserved for displaying the parameter value reading as received by the controller module.

In a particular embodiment, the default LCD message displayed is flow rate and power on the first display line and the percent of capacity or time remaining for each battery connected on the second display line. Alternately, if the flow meter 124 is disabled, motor speed and motor power may be displayed on the first display line. If the controller module is coupled to the CDAS, the LCD displays "DAS CONNECTED." Other main LCD messages displayed include "PERFORMING SELF TEST," and "VAD SYSTEM MODEL NUMBER," which are toggled upon initial power-up while the microprocessor executes the self test sequence.

The controller module 16 is also capable of displaying diagnostic messages on the LCD 128. A user may scroll the diagnostic messages by pressing the display scroll keypad switch 130. The first depression of the display scroll key initially illuminates the backlight (if not previously lit), and all subsequent scroll key depressions continuously scan through the message displays. Diagnostic messages included in a particular embodiment of the invention include the date, time and unit serial number; motor current; motor speed; received amplitudes of the flow sensor channels; excess suction enabled (or disabled); flow sensor enabled (or disabled) and physiological control enabled (disabled).

The controller module 16 also provides audible alarms and alarm messages, which are displayed on the LCD. The audible alarm may use different distinct sounds to indicate diagnostic and emergency events. The diagnostic alarm may have multiple volume levels and may repeat a series of beeping tones which increase in rate and volume until answered by pressing the alarm silence key. Pressing the alarm silence key silences the audible alarm, but does not clear the alarm message displayed on the LCD 128. In general, diagnostic alarms are provided when a measured parameter (PARAMETER) differs from a predetermined parameter value (PARAMETER$_{alarm}$) by a threshold amount. The PARAMETE$_{alarm}$ and threshold values are stored in the EEPROM. The EEPROM provides non-volatile storage for these important messages and system parameters. The emergency audible alarm may comprise a continuous beep at maximum volume level to indicate the severity of the event. If both diagnostic and emergency events occur simultaneously, the microprocessor is programmed to sound only the emergency alarm.

The microprocessor is programmed to store some alarm messages in the controller module 16 until acknowledged by an operator via the CDAS 18. In an embodiment of the invention, the selected alarm message and a time stamp for the message are stored until acknowledged by the CDAS 18. The alarm displays in conjunction with the data regarding system parameters associated with the first and last predetermined pump event stored in the memory device 122 insure that ample data exists for analysis by a physician or technician.

The multicolored battery status LEDs 132 may indicate various battery conditions. For example, a solid green indicates that the battery is in use and blinking amber indicates a low charge level, expired battery, or battery disconnected. If the battery status LED is off, the charged battery is connected but not presently in use, and alternating amber and green indicates the self test mode. The safe mode indicator 134 is activated by the watchdog timer 94 in the event of a microcontroller 80 failure. Emergency alarms and diagnostic alarms for an embodiment of the invention are displayed in Table 1 and Table 2 below.

TABLE 1

Emergency Alarms

| Alarm condition | Message | Notes |
|---|---|---|
| Pump stopped | PUMP STOPPED | |
| Controller failure | CONTROLLER FAILURE | Results in safe mode pump speed setting |
| Both batteries disconnected | BOTH BATTERIES DISCONNECTED | |
| Patient interface disconnected | VAD DISCONNECTED | |

TABLE 2

Diagnostic Alarms

| Alarm condition | Message | Notes |
|---|---|---|
| Excess current | EXCESS CURRENT | Motor current > I$_{alarm}$ |
| Low flow rate | REDUCED FLOW RATE | <2 liters/minute |
| Internal battery low | LOW INTERNAL BATTERY | |
| Low Motor Speed | MOTOR SPEED REDUCED | Motor RPM < RPM$_{alarm}$ |
| Pump restarted | PUMP RESTARTED | |
| Excess suction | EXCESS SUCTION RPMS REDUCED | |
| Battery #1 disconnected | BATTERY #1 DISCONNECTED | Battery indicator #1 flashes amber |
| Battery #1 discharged | BATTERY #1 DISCHARGED | Battery indicator #1 flashes amber |
| Battery #1 expired | BATTERY #1 EXPIRED | Battery indicator #1 flashes amber |
| Battery #2 disconnected | BATTERY #2 DISCONNECTED | Battery indicator #2 flashes amber |
| Battery #2 discharged | BATTERY #2 DISCHARGED | Battery indicator #2 flashes amber |
| Battery #2 expired | BATTERY #2 EXPIRED | Battery indicator #2 flashes amber |

Clinical Data Acquisition System (CDAS)

Figure 9:
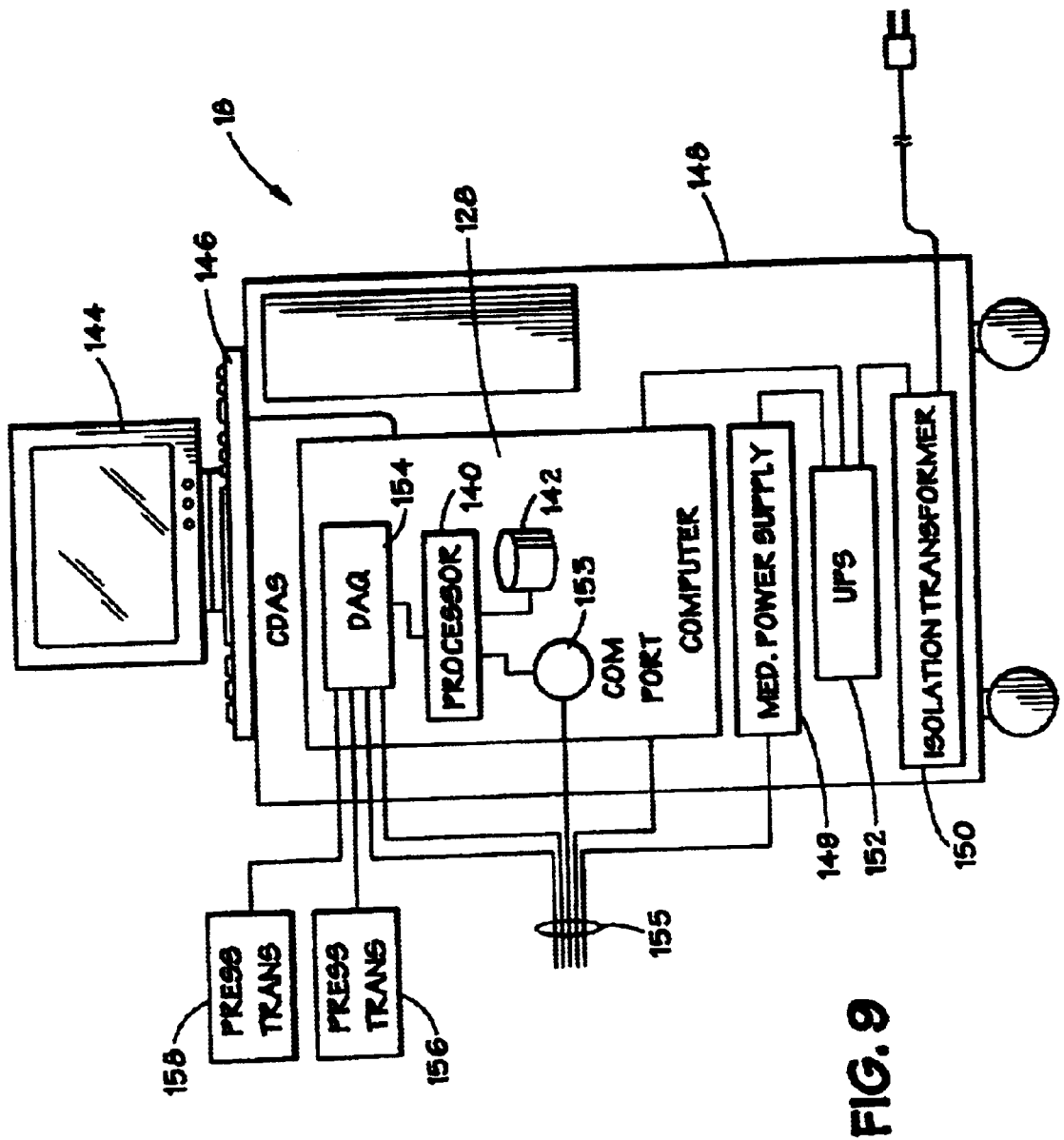
FIG. 9 illustrates an embodiment of a clinical data acquisition system in accordance with the invention.

An embodiment of the CDAS 18 is pictured schematically in FIG. 9. The CDAS includes a computer 128, which includes a processor 140, at least one memory storage device 142, a video display 144 and an input device 146, such as a computer keyboard. In one embodiment, the video display 144 is an LCD. The CDAS 18 is mounted on a moveable cart 148 such that the CDAS 18 can escort a patient during movements within the hospital. The CDAS 18 is configured for use within a hospital setting, and is not intended to go home with a patient having an implanted pump 12. The CDAS 18 further collects and displays data from the controller module 16, sends comments and data to the controller module 16, and supplies power to the controller module 16.

The primary power source for the CDAS 18 is 120 volt, 60 Hz AC power, or 220 volt, 50 Hz AC power as from standard wall electrical outlets. The CDAS 18 includes a medical grade power supply 149 such as is known in the art for providing power to the controller module 16. The AC mains are isolated by a medical grade isolation transformer 150. The CDAS 18 further includes a battery backed uninterruptable power supply (UPS) system 152. In one embodiment of the invention, the UPS 152 is capable of operating the controller module 16 alone for eight hours and the controller module 16 and CDAS 18 for one hour when AC power is unavailable.

The CDAS 18 provides an operator interface to the controller module in addition to the LCD 128 and controller module keypad 130. The CDAS 18 includes a communications port 153, such as a standard RS-232 communications port and an A/D converter 154. All data communication between the CDAS 18 and the controller module 16 is electrically isolated. A cable 155 couples the CDAS 18 to one of the controller module connectors 24, 26, through which the CDAS 18 provides power and communicates with the controller module 16. The cable 155 connects the CDAS power supply 149 to the battery detect circuit 100,102 associated with the appropriate controller module connector 24, 26. The same cable 155 additionally couples the communications port 153 to the RS-232 driver/receiver 81 and the digital to analog converter 154 to the flow meter 124 and the motor controller 84.

Thus, the CDAS 18 is able to exchange commands and other information with the controller module 16, such as digital data stored in the parameters and messages EEPROM 98 or the controller module memory devices 122. Further, the CDAS 18 is directly coupled to the motor controller 84 and the flow meter 124 to receive real-time analog motor current and flow data, respectively. The real-time analog data received may be isolated and filtered, then displayed in real time on the CDAS video display 144.

In an embodiment of the invention, digital data regarding pump voltage, current, RPM and flow data are stored in the controller module memory device 128 and are downloaded to the CDAS 18 via the RS-232 interface. The CDAS 18 may then plot this information on the video display 144, and store the data in the CDAS memory device 142. Further, diagnostic and emergency messages may be downloaded and a log kept of these messages. The CDAS 18 is also coupled to the controller module real-time clock and calendar 82 so that these parameters may be synchronized with the controller module 18.

The CDAS 18 may further be coupled to other devices external to the controller module 16. Examples of such devices may include an ex-vivo blood pressure transducer for capturing and displaying blood pressure information during surgery. An auxiliary contact microphone 158 may be coupled to the CDAS 18 to capture and display acoustic information for monitoring pump 12 condition. Thus, data in addition to that provided by the controller module 16 may be captured, stored, and displayed by the CDAS 18.

The CDAS 18 further provides an interface for an operator to change system parameters such as pump speed, alarm thresholds and excess suction parameters, and to run test routines on the system. In an embodiment of the invention, the system access is password controlled based on different user levels. For example, Level 1 users (patient) may be allowed to view alarm messages and pump operating parameters; Level 2 users (physician) may view alarm messages and pump operating parameters, and also make minor system changes such as adjusting pump speed; and Level 3 users (technician) have access to all CDAS functionality.

Another function related to the CDAS 18/controller module 16 interface involves diagnosing pump 12 problems. As discussed above, pump parameters are stored for a predetermined time period prior to two emergency events in the controller module memory. If, for example, the pump 12 fails while the controller module 16 is not connected to the CDAS 18, 55 seconds of pump performance data is stored in the controller module memory 122. When the controller module 16 is coupled to the CDAS 18 subsequent to the failure, analysis of the pump parameters just prior to the failure may be essential for diagnosing the problem.

Examples of additional controller module 16 operations performed via the CDAS 18 in an embodiment of the invention include programming and verifying multilingual controller module LCD messages, real-time clock/calendar, parameters for use by the excess suction feature, alarm parameters, and operational parameters. Further, a user may operate the pump motor, the excess suction feature, and the flow meter via the CDAS, or closed loop physiological system control may be activated.

Patient Home Support System (PHSS)

Known artificial heart and VAD systems rely on a large external console for the bulk of the system operation. In the system of an embodiment in accordance with the present invention, the controller module includes processing, memory, and operator interface capabilities. Thus, the system 10 may be operated for an extended period independent of the CDAS 18 in a truly portable mode.

Figure 10:
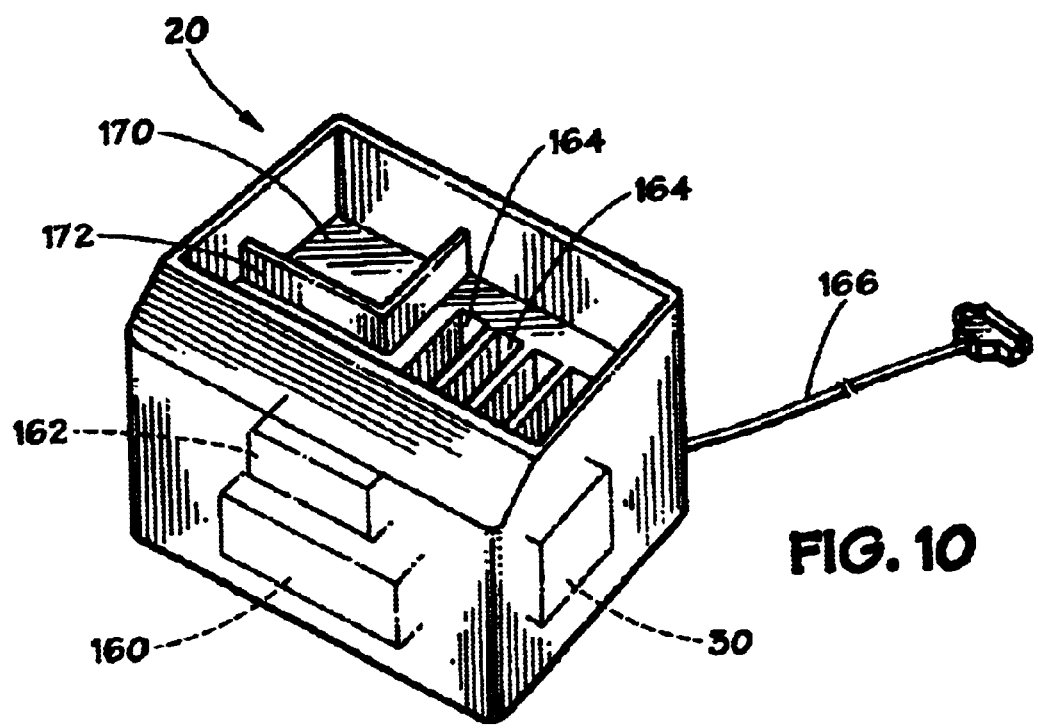
FIG. 10 illustrates an embodiment of a patient home support system in accordance with the invention.
Figure 5:
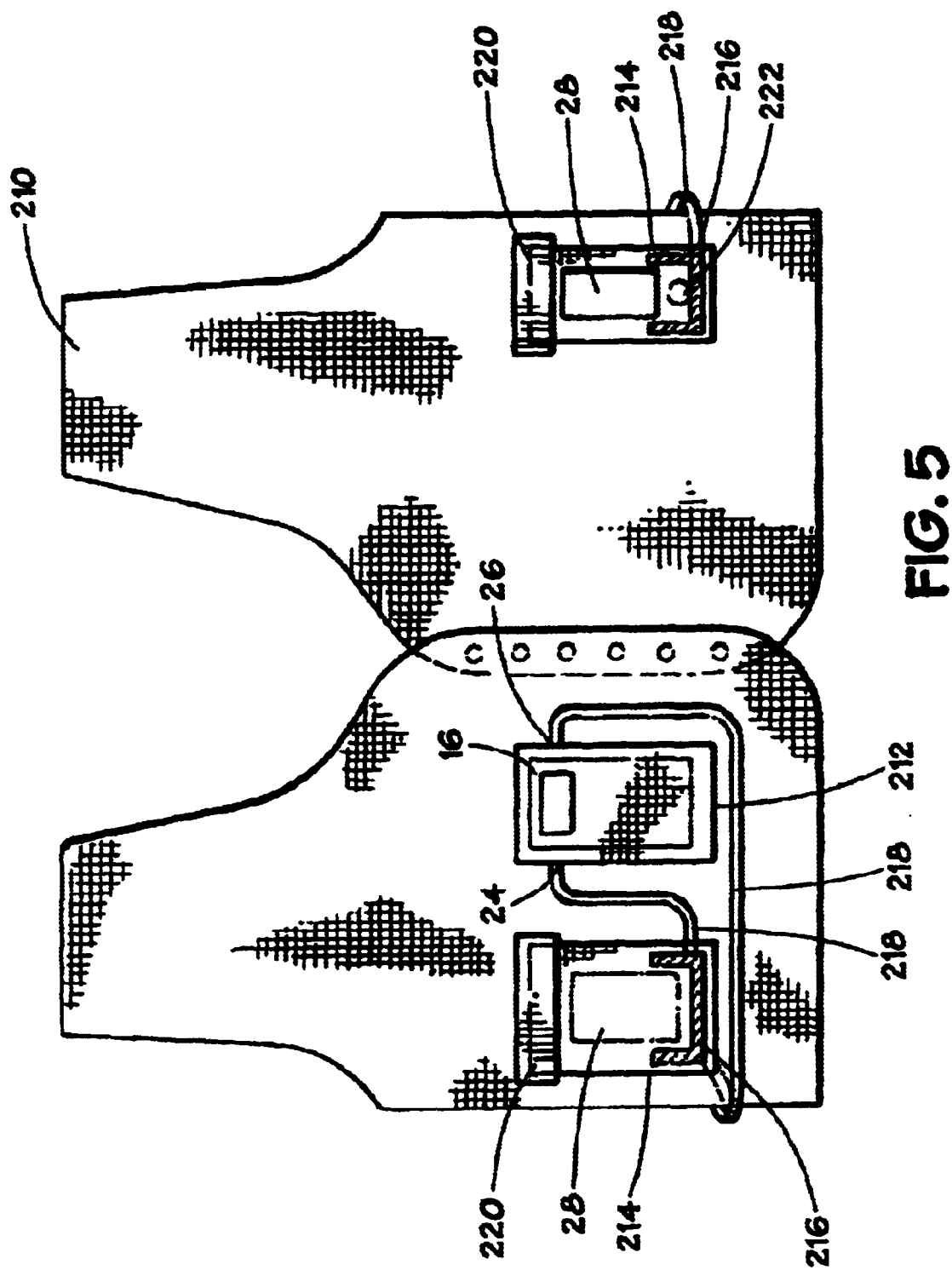

The PHSS 20 of an embodiment of the invention is illustrated in FIG. 10. The PHSS 20 is a portable device that can be hand-carried, as opposed to being moved on a cart as the consoles of prior art VAD systems. The PHSS 20 comprises a power supply 160 sourced by 120 volt, 60 Hz AC power or 220 volt, 50 Hz AC power as from standard wall electrical outlets. The AC mains are isolated by a medical grade isolation transformer 162. The PHSS further includes at least one compartment 164 having a connector (not shown) for receiving one or more batteries 28. In an embodiment of the invention, the PHSS includes four battery compartments 164, each of the compartments 164 being coupled to an integral battery charger 30.

Figure 11:
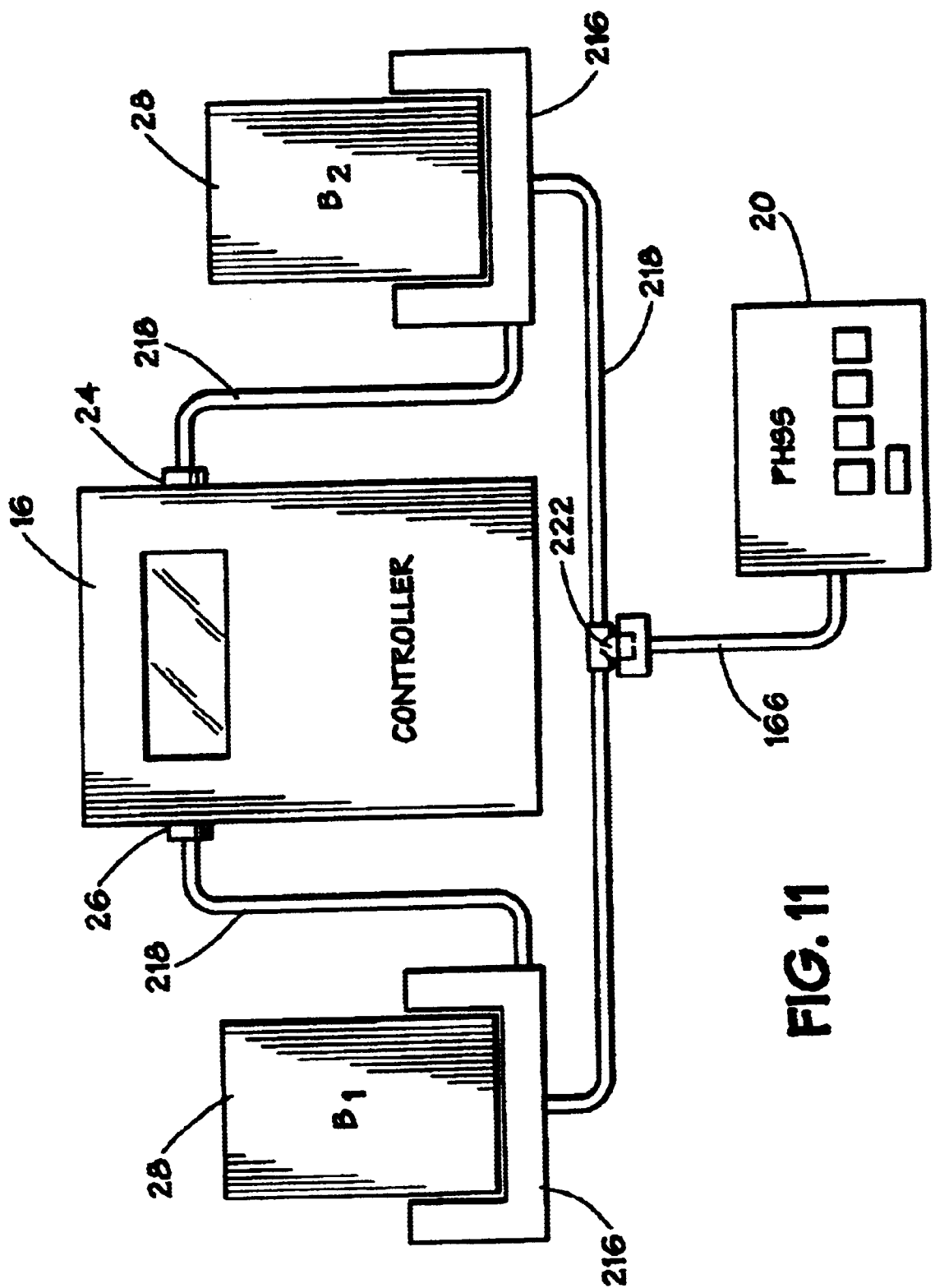
FIG. 11 illustrates an exemplary PHSS connection system in accordance with the invention.

The PHSS 20 is coupled to the controller module 16 via a cable 166. FIG. 11 illustrates the PHSS 20 connection to the controller module for one embodiment of the invention. The PHSS cable 166 is coupled to the PHSS connector 222, which may be connected directly to one of the battery connectors 216 or connected to a cable 218 between the battery connectors 216. The battery connectors 216 are coupled to the controller module connectors 24, 26. When the PHSS 20 is coupled to the controller module 16, the DASPRES1 or DASPRES2 signal of the power control circuit 104 will be logically high. Therefore, the power control circuit 104 will power the controller module 16 from the PHSS power supply. The controller module 16 will then attempt to communicate via the RS-232 interface with the connected device. Since the PHSS 20 does not include communications capabilities, the controller module 16 then knows that the PHSS 20 is connected rather than the CDAS 18.

The PHSS connector 222 further includes a logic device or circuit (not shown) for further managing the system power when the PHSS 20 is coupled to the controller module 16. When the PHSS cable 166 is coupled to the PHSS connector 222, the controller module 16 is powered via the PHSS. Once the PHSS power connection is established, the batteries 28 may be removed from the battery connectors 216. A message noting that it is safe to remove the batteries may be displayed on the LCD 128.

The batteries 28 are then placed in the battery compartments 164, where they either provide a back-up to the PHSS 20, or they are recharged by the charger 30 contained within the PHSS 20. Using the batteries 28 as a power back-up eliminates the need for an additional back-up power supply, in turn reducing the size requirement and making the PHSS more economical. The PHSS connector 222 queries the batteries 28 held in the compartments 164 to determine their respective charge levels. In one embodiment, the battery with the highest charge provides a power back-up to the PHSS. The remaining battery is recharged. If the recharging battery's charge level reaches a point higher than the back-up battery 28, PHSS connector 222 reverses the battery 28 function so the back-up battery 28 may now recharge.

The remaining battery compartments 64 may hold additional spare batteries, which are either recharged or provide back-up to the PHSS power supply as determined by the logic circuit within the PHSS connector 222. The PHSS further includes an additional compartment 172 for holding a spare controller module (not shown), and a storage space 170 for holding spare cables and the like.

The above description of exemplary embodiments of the invention are made by way of example and not for purposes of limitation. Many variations may be made to the embodiments and methods disclosed herein without departing from the scope and spirit of the present invention. The present invention is intended to be limited only by the scope and spirit of the following claims.

What is claimed is:

1. A method of controlling an implanted pump comprising the acts of:

coupling a controller module to the implanted pump, the controller module including a processor, a display device, a user input device, and a digital memory having a first memory segment including a circular buffer and a second memory segment;

collecting operating parameters of the implantable pump;

displaying the collected parameters on the display device as selected via the user input device;

storing the collected parameters in the first memory segment;

continuously updating the stored operating parameters of the implanted pump such that a predetermined time period of the most recent data are stored in the first memory segment;

transferring a predetermined time period of the stored parameters from the first segment to the second segment upon pump failure; and displaying the stored parameters on the display device as selected via the user input device.

2. The method of claim 1 further comprising the acts of:

providing a data acquisition system including a video display device;

transferring the collected parameters from the controller module to the data acquisition system; and displaying the collected parameters on the data acquisition system video display device.

3. The method of claim 2 further comprising the data acquisition system including a memory storage device, the method further comprising the acts of:

transferring the collected parameters stored in the controller module first memory segment to the data acquisition system memory storage device; and displaying the collected parameters from the data acquisition system storage device on the video display device.

4. The method of claim 1 wherein the digital memory includes a third memory segment, further comprising the act of transferring the predetermined time period of the stored parameters from the first segment to the third segment upon a subsequent predetermined event.

* * * * *